United States Patent [19]

Weaver et al.

[11] Patent Number: 4,578,451
[45] Date of Patent: Mar. 25, 1986

[54] SURGICAL FILAMENTS FROM BLOCK COPOLYETHERAMIDES

[75] Inventors: Gregory A. Weaver, Neshanic Station; Lester F. Price, Matawan; Crawford R. Britt, Plainfield; W. Shalaby Shalaby, Lebanon, all of N.J.

[73] Assignee: Ethicon, Inc., Somerville, N.J.

[21] Appl. No.: 514,371

[22] Filed: Jul. 15, 1983

[51] Int. Cl.$^4$ .................. C08G 69/40; A61L 17/00
[52] U.S. Cl. .................. 528/292; 128/335.5; 528/326
[58] Field of Search ............ 128/335.5; 528/292, 528/420, 434, 437, 184, 326; 264/235, 235.6, DIG. 28; 523/113; 204/159.19; 525/408

[56] References Cited

U.S. PATENT DOCUMENTS

| | | | |
|---|---|---|---|
| 2,216,835 | 10/1940 | Carothers | 528/301 |
| 3,044,987 | 7/1962 | Schaefgen et al. | 528/367 |
| 3,384,681 | 5/1968 | Kobayashi et al. | 528/211 |
| 4,209,607 | 6/1980 | Shalaby et al. | 528/291 |
| 4,224,946 | 9/1980 | Kaplan | 128/335.5 |
| 4,246,904 | 1/1981 | Kaplan | 128/335.5 |
| 4,314,561 | 2/1982 | Kaplan | 128/335.5 |
| 4,343,931 | 8/1982 | Barrows | 528/291 |
| 4,361,680 | 11/1982 | Borg et al. | 525/437 |
| 4,438,240 | 3/1984 | Tanaka et al. | 528/301 |

*Primary Examiner*—Veronica P. Hoke
*Attorney, Agent, or Firm*—Charles J. Metz

[57] ABSTRACT

Surgical filaments such as sutures and ligatures are produced from block copolyetheramides. The filaments combine high strength with high compliance.

15 Claims, No Drawings

SURGICAL FILAMENTS FROM BLOCK COPOLYETHERAMIDES

The invention relates to surgical filaments such as sutures and ligatures that are very strong, but which are limp and have high compliance. The surgical filaments are made from block copolyetheramides.

BACKGROUND OF THE INVENTION

A number of synthetic thermoplastic polymers are employed in the production of surgical filaments such as sutures and ligatures. Such polymers include nylon, polyester, and polypropylene. In the preferred form, a surgical filament is employed in the form of a monofilament, if that is possible, because monofilaments are easy to draw through tissue and have lower tissue reaction than do braided filaments. However, many of the synthetic thermoplastic polymers that are employed as surgical filaments are too stiff or non-compliant to be used in the form of monofilaments.

Polypropylene is the leading synthetic thermoplastic polymer that is employed in the form of a monofilament surgical suture. However, the properties of polypropylene are such that, especially with the larger sizes such as 2/0 and higher, the compliance is just adequate for the suture to be employed in the form of a monofilment. Thus, there has been an extensive search for a synthetic thermoplastic polymer that is strong, but yet is quite compliant so that it can readily be employed in the form of a monofilament.

One solution to this problem is proposed in U.S. Pat. No. 4,224,946, which describes a monofilament suture composed of a polyether-polyester block copolymer. For instance, a preferred version is a polyalkylene terephthalate block alternating with a polyoxytetramethylene block. An earlier proposed solution for the problem of low compliance with monofilament sutures was made in U.S. Pat. No. 3,454,011, in which it was proposed to use Spandex polyurethane block copolymers as monofilament surgical sutures. A typical Spandex polyurethane block copolymer contains a urethane block alternating with a block of polyoxytetramethylene ether. However, it was found that such sutures were too elastic, and therefore, did not find general acceptance in the medical profession.

Thus, the prior art is aware of at least two types of block copolymers that employ polyoxytetramethylene ether blocks alternating with other types of blocks, which were proposed as flexible monofilament surgical filaments. In the case wherein the polyether blocks alternated with polyurethane blocks, the sutures were too elastic and have not been commercially successful. In the case of the block copolymers wherein the polyether blocks alternated with polyester blocks, the technology is too new to determine whether or not such sutures will find general acceptance. Therefore, we have the situation where one type of block copolymer containing a polyether block was found not to be acceptable as a surgical suture, and another type of block copolymer containing a similar polyether block wherein it does not appear that such block copolymers will make acceptable surgical sutures; although it is too soon to give an assessment of the commercial acceptability of such sutures.

This invention relates to surgical filaments made from a block copolyetheramide wherein the filaments are quite strong, and yet are highly compliant, and therefore appear to be an excellent solution to the desire in the profession for having a monofilament suture that is both strong and compliant.

BRIEF SUMMARY OF THE INVENTION

The invention provides a drawn, highly oriented, strong, compliant surgical filament comprising a block copolyetheramide. The block copolymers that are contemplated for use in the invention are illustrated by preferred embodiments wherein the polyamide blocks are bonded to the polyether blocks through ester or amide groups, and wherein the polyamide blocks are derived from $C_6$ to $C_{12}$ omega-amino-acids or lactams or from the reaction product of a $C_6$ to $C_{12}$ diacid with a $C_6$ to $C_{12}$ diamine, and wherein the polyether block is a polyalkylene ether wherein the individual alkylene groups are $C_2$ to $C_6$ polymethylene, and more preferably $C_3$ to $C_6$ polymethylene.

THE PRIOR ART

The manufacturer of one class of block copolyetheramides has recommended them for use in a wide variety of applications, ranging from adhesive compositions to extruded and molded articles, including textile monofilaments. For instance, reference is made to Borg et al., U.S. Pat. No. 4,361,680, in which the use of polyamide-polyether block copolymers in adhesive compositions is disclosed.

DETAILED DESCRIPTION OF THE INVENTION

The block copolyetheramides that are employed in the invention are a known class of polymers. They are copolymers that contain at least one polyamide block linked chemically to at least one polyether block.

The copolymers contain random sequences of polyether and polyamide blocks of varying chain lengths. The exact molecular (or polymeric chain) structure cannot be described with specificity, in most cases. Also, the particular molecular structure can be dependent upon the method of preparation of the block copolymer. For instance, if the polymer is produced by linking together already formed functional chains of polyether to polyamide (i.e., such chains having reactive end groups), then the polymeric structure will tend to be an —A—B)$_n$ type block copolymer. And when the polymer is produced by using a polyether as a starter or initiator for polymerizing a lactam, then the polymeric structure will tend to be a mixture of A—B—A and A—B type block copolymers, wherein the B segments represent polyether blocks. However, one cannot exclude the possibility that other polymer chain types will be present in small amounts, including small amounts of each type of homopolymer.

One preferred way of producing the block copolymers used in the invention is to use a polyether oligomer (m.w. of about 200 to 6000, and preferably from about 500 to 3000), as a prepolymer or starter for the polymerization of a lactam or an omega-aminoacid. The polyether is preferably amine-terminated. Amine-terminated polyethers can be produced from polyether glycols by standard organic synthesis techniques. Two illustrations are the following:

(a) React the polyether glycol with acrylonitrile to form the corresponding nitrile-terminated polyether, which is then reduced to the primary amine; and (b) React the polyether glycol with an organic diisocyanate to form an isocyanato-terminated polyether, which is then hydrolyzed to form the primary amine.

The reaction between the amine-terminated polyether and a lactam (or a mixture of a lactam and an omega amino acid) proceeds quite readily. A small amount of catalyst, such as dilute aqueous phosphoric acid, can be used, if desired, but the amino groups of an amino acid can initiate the reaction, so additional catalysts need not be used. This reaction is a known type. For instance, see Shalaby et al., "Copolymerization of Caprolactam with Polyoxybutylene Diamine", Polymer Engineering And Science, March, 1973, Vol. 13, No. 2, pages 88-95, and Shalaby et al., "Nylon 12-Poly(oxybutylene) Block Copolymers", Ind. Eng. Chem. Res. Develop., Vol. 12, No. 2, June 1973, pages 128-132.

Another way to produce the block copolyetheramides used in the invention is to react a polyether glycol with a carboxyl-terminated polyamide oligomer having a molecular weight of from about 300 to about 10,000, and preferably from about 800 to about 5,000. This is also a known type of reaction. For instance, see Borg et al., U.S. Pat. No. 4,361,680.

Another known type procedure is to react a polyamide, a polyether glycol, and a diacid such as adipic acid.

As a general rule, the block copolymer used in the invention will contain from about 50 to about 90 weight per cent polyamide, and from about 50 to about 10 weight per cent polyether moieties, based on weight of polyamide plus polyether segments in the copolymer (that is, ignoring the weight of any linking groups, which is usually minor).

The monomeric units used, either singly or in mixtures thereof, to make the polyamide segments are illustrated by laurolactam, omega-amino-undecanoic acid, epsiloncaprolactam, adipic acid, sebacic acid, 1,6-diaminohexane, 1,12-diaminododecane, and the like.

The polyethers used to make the polyether segments are derived from polyether glycols wherein the individual ether units are $C_2$ or higher oxyalkylene, preferably wherein the alkylene groups are straight chain groups. Polyoxybutylene glycol is the preferred polyether.

The polyether block can be a co-polyether, that is, it can contain two or more different types of oxyalkylene groups.

In some cases, it may be desirable to incorporate in the polymeric chain a small proportion of groups (e.g., from 1 to 10 weight per cent) that contain pendant substituents which act to make the surgical filaments of the invention more flexible and/or compliant. Such groups include alkyl- or 2-alkenyl-substituted succinate wherein the alkyl or 2-alkenyl groups have from 4 to 30, and preferably from 12 to 22, carbon atoms, dimer acid ester groups, various carboxylated long chain hydrocarbons that can be derived from dimer acid, and the like. The groups having pendant substitutents can be incorporated in the polymeric chain by known synthetic techniques.

The properties required for successful utility as a surgical filament will, to a limited extent, dictate the specific block copolymers that are preferred for use in the invention. Such properties include:

(1) Adequate tensile properties, e.g., straight tensile strength of at least 40,000 psi and knot strength of at least 30,000 psi;
(2) Elongation of less than 100% (so that the filament is not too stretchy); and
(3) Substantial retention of tensile properties in vivo.

Among the characteristics of the polymer that contribute to one or more of these desirable suture porperties are:

(a) A molecular weight high enough that the polymer has an inherent viscosity of at least 0.6, and preferably between 1 and 2, in the common polyamide solvents such as m-cresol, trifluoracetic acid, or trifluoroethanol.
(b) At least about 50 weight per cent of the block copolymer being polyamide segment(s); and
(c) Avoidance of a substantial proportion of hydrophilic groups such as polyoxyethylene groups.

The sutures of the invention can be attached to surgical needles at at least one end, they can be sterilized in the usual manner (as by ethylene oxide or gamma radiation), and they can be made in the usual sizes (e.g., from 2 to 7-0 or smaller). The following examples illustrate various aspects of the invention:

EXAMPLES 1-5

In these Examples, the block copolyetheramide employed was "PEBAX" 5533 SN 00, manufactured by Ato Chimie of Courbevoie, France. This copolymer can be represented by the formula:

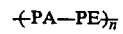

wherein PA represents a polyamide block derived from dodecalactam, using a diacid such as adipic acid as a coreactant, wherein PE represents a polyoxytetramethylene block derived from polyoxytetramethylene glycol, wherein n represents a number whose average value reflects the degree of polymerization, wherein the PA segments constitute about 64 weight per cent of the polymer, wherein the PE segments constitute about 36 weight per cent of the polymer, and wherein the PA segments are linked to the PE segments through ester groups. The polymer has the following properties:

TABLE I

| | |
|---|---|
| Density, ASTM D 792 | 1.01 |
| Melting Point, ASTM D 789 | 168° C. |
| Melting Point, Hot Stage Thermal Microscopy | 159-160° C. |
| Melt Index, ASTM D 1238, 235° C./1 kg. | 8 |

This polymer is made into size 4/0 monofilament suture material in accordance with the extrusion and drawing conditions outlined below:

| Extrusion: (Screw extruder, 1" diameter, 12/1 L/D) | |
|---|---|
| Block/die temp | 466/485° F. |
| Die diam./# holes | 0.054"/4 (1 end taken up) |
| Barrel pressure | 1150 psi |
| Pump pressure | 1530 psi |
| Shear rate | 170 sec$^{-1}$ |
| Throughput | 210 gph/hole (840 gph total) |
| Quench water temp | 75° F. |
| Drawing: | |
| 1st godet speed/temp | 25 fpm/200° F. |
| 2nd godet speed/temp | 98 fpm/165° F. |
| 3rd godet speed/temp | 150 fpm/ambient |
| heated oven temp | 255° F. |
| 4th godet speed/temp | 200 fpm/ambient |

The first godet takes up the extruded monofilament from the quench bath. The "jet stretch" or "drawdown"(i.e., ratio of peripheral speed of the first godet to the speed of the monofilament as it comes out of the extruder) is about 4×. There is a heated oven located between the third and fourth godets. The overall draw ratio (that is, the ratio of the peripheral speeds of the last godet to the first godet) has not been found to be narrowly critical. Useful draw ratios are usually between 4× and 12×, and preferably between 6× and 10×. The drawing temperatures can vary widely, e.g., from ambient (i.e., about 20°–25° C.) up to about 80°–100° C.

Representative properties of five sample runs, as drawn, are displayed in Table II, below:

TABLE II

| Example No. | 1 | 2 | 3 | 4 | 5 |
|---|---|---|---|---|---|
| Diameter; mils | 8.2 | 9.0 | 8.4 | 8.0 | 7.9 |
| Draw ratio[(1)] | 8X | 7X | 7.5X | 8X | 8X |
| Elongation; % | 30 | 41 | 51 | 31 | 35 |
| Straight Tensile Strength; | | | | | |
| lb | 6.1 | 6.2 | 6.4 | 6.0 | 6.1 |
| psi | 115,600 | 97,400 | 115,400 | 119,300 | 124,400 |
| Knot Tensile Strength; | | | | | |
| lb | 3.5 | 4.6 | 3.3 | 3.2 | 3.4 |
| psi | 66,200 | 72,300 | 59,500 | 63,600 | 69,300 |
| Young's Modulus; psi | 103,000 | 109,000 | 110,000 | 147,000 | 134,000 |

[(1)]In Examples 2 and 3, the 4th godet speeds are 175 and 187½ feet per minute, respectively, which yield draw ratios of 7X and 7.5X, respectively.

Samples of the monofilament of Example 5 were annealed in a forced nitrogen oven at the two annealing conditions shown below. Representative properties of these annealed monfilaments are displayed below in Table III:

TABLE III

| ANNEALED SUTURE PROPERTIES | | |
|---|---|---|
| | Knot | Straight |
| A. 0% Relax at 66° C. for 16 hours | | |
| Diameter | 8.2 | |
| Knot Tensile Strength | 3.5 lbs. | |
| Elongation | 29% | |
| Intrinsic Value | 66,000 psi | |
| B. 5% Relax at 66° F. for 16 hours | | |
| Diameter | 8.2 | 8.2 |
| Tensile | 3.5 lbs. | 5.7 lbs. |
| Elongation | 27% | 28% |
| Intrinsic Value | 66,000 psi | 108,000 psi |
| Young's Modulus | — | 130,000 psi |

It is preferred that the surgical filaments of the invention be annealed in order to develop optimum properties such as high tensile strength and resistance to shrinkage upon exposure to moderately elevated temperatures of, e.g., 50° to 60° C., which can readily be encountered during packaging and storage.

The annealing is usually carried out at a temperature within the range of from about 60° to about 140° C. for a period of from about 2 to about 16 hours, and preferably at a temperature within the range of from about 110° to about 130° C. for about 3 to 8 hours. The filaments can be permitted to relax or shorten their length during the annealing, up to about a 10 per cent reduction in length.

EXAMPLE 6

Examples of the monofilament of Example 5 are annealed with 5% relax (i.e., 5% reduction in length) in a forced nitrogen oven at 120° C. for four hours. The annealed monofilaments are then sterilized by exposure to 2.5 Mrad of gamma radiation from a $^{60}$Co Source.

The properties of the monofilaments, as drawn, annealed, and annealed plus sterilized, are displayed below in Table IV:

TABLE IV

| Monofilament Properties | | | |
|---|---|---|---|
| | As Drawn | Annealed | Annealed and Sterilized |
| Diameter, mils | 7.9 | 8.1 | 8.0 |
| Tensile, lbs | 6.1 | 5.7 | 4.6 |
| psi | 124,000 | 111,000 | 92,000 |
| Knot strength, lbs | 3.4 | 3.2 | 2.9 |
| psi | 69,000 | 62,000 | 58,000 |
| Elongation, % | 35 | 38 | 35 |
| Young's Modulus, psi | 134,000 | 115,000 | 130,000 |

EXAMPLE 7

The block copolyetheramide described above in Examples 1–5 is made into size 2/0 monofilament suture material by extruding and drawing under the following conditions:

TABLE V

| Extrusion: (Screw extruder, 1" diameter, 12/1 L/D) | |
|---|---|
| Block/die temp | 475/475° F. |
| Die diam./holes | 0.08"/1 |
| Barrel pressure | 1150 psi |
| Pump pressure | 600 psi |
| Shear rate | 125 sec$^{-1}$ |
| Throughput | 465 grams per hole/hr. |
| Quench water temp | 75° F. |
| Jet stretch | 4X |
| Drawing: | |
| 1st godet speed/temp | 25 fpm/ambient |
| 2nd godet speed/temp | 98 fpm/165° F. |
| 3rd godet speed/temp | 150 fpm/ambient |
| heated oven temp | 255° F. |
| 4th godet speed/temp | 200° fpm/ambient |

Representative properties of these monofilaments, as drawn, are shown in Table VI:

TABLE VI

| Sample No. | 1 | 2 | 3 |
|---|---|---|---|
| Diameter, mils | 12.8 | 12.8 | 12.8 |
| Draw ratio | 8X | 8X | 8X |
| Elongation, % | 68 | 66 | 62 |
| Straight Tensile | | | |
| Strength, lb | 12.2 | 13.1 | 12.9 |
| psi | 94,800 | 101,800 | 100,250 |
| Knot Tensile | | | |
| Strength, lb | 6.5 | 7.0 | 6.8 |
| psi | 50,600 | 54,400 | 52,800 |
| Young's Modulus, psi | 100,000 | 114,000 | 110,000 |

EXAMPLE 8

In order to investigate the effect of different annealing conditions on the final properties of monofilament suture material, samples of the monofilament described above as Example 4 (Table II) are annealed at various conditions, and are then tested for several physical properties. The results are displayed below in Table VII, which shows the annealing conditions and representative physical properties:

TABLE VII

| Sample No. | 1 | 2 | 3 | 4 | 5 | 6 |
|---|---|---|---|---|---|---|
| Annealing | | | | | | |
| Temp., °C. | 120 | 120 | 100 | 124 | 80 | 140 |

TABLE VII-continued

| Sample No. | 1 | 2 | 3 | 4 | 5 | 6 |
|---|---|---|---|---|---|---|
| % Relax | 0 | 0 | 0 | 0 | 0 | 0 |
| Time, hrs. | 16 | 3 | 3 | 6 | 3 | 3 |
| Properties |  |  |  |  |  |  |
| Diameter, mils | 8.0 | 8.5 | 8.6 | 8.1 | 8.35 | 8.2 |
| Straight Tensile Strength, |  |  |  |  |  |  |
| lbs. | 5.1 | 6.4 | 6.2 | 6.1 | 6.1 | 5.6 |
| psi | 101,400 | 112,000 | 107,000 | 118,000 | 110,000 | 103,000 |
| Knot Tensile Strength, |  |  |  |  |  |  |
| lbs. | 3.0 | 3.4 | 3.1 | 3.3 | 3.2 | 3.7 |
| psi | 59,600 | 60,000 | 53,000 | 64,000 | 58,000 | 68,000 |
| Elongation, % | 45 | 47 | 47 | 36 | 46 | 47 |
| Young's Modulus, psi | 111,000 | 93,000 | 124,000 | 105,000 | 128,000 | 95,000 |
| Free Shrinkage, %[1] | — | 6.5 | 9.5 | 6.3 | 15 | 2.9 |

[1] Percent reduction in length after a 24-inch sample is placed in an oven at 140° F. for 20 minutes and allowed to shrink.

As the examples illustrate, the surgical filaments of the invention combine high straight tensile strength with good compliance, as is illustrated by low Young's modulus values. The filaments, both as drawn and after annealing, exhibit straight tensile strengths of over 50,000 psi, in preferred embodiments over 75,000 psi, and in more preferred embodiments over 100,000 psi, and Young's modulus values of below 250,000 psi, in preferred embodiments below about 200,000 psi and in more preferred embodiments below 150,000 psi.

The straight tensile strength values reported herein were determined by an Instron Tensile Tester using a two-inch gauge length, a chart speed of 10 inches per minute, and a cross-head speed of two inches per minute. The Young's modulus was determined by standard procedures from the initial portion of the stress-strain curve.

The surgical filaments of the invention are primarily intended for use as surgical sutures and ligatures, but they may also be fabricated into fibrous prostheses such as vascular graft materials and the like.

What is claimed is:

1. In a surgical filament comprising a drawn and oriented polymer, the improvement which comprises using as the polymer a block copolyetheramide consisting essentially of (a) polyamide blocks derived from $C_6$ to $C_{12}$ aliphatic omega-amino-acids of lactams or the reaction product of a $C_6$ to $C_{12}$ aliphatic diacid with a $C_6$ to $C_{12}$ aliphatic diamine, and (b) polyether blocks consisting essentially of polyalkylene ethers wherein the individual alkylene groups are $C_2$ to $C_6$ polymethylene, wherein said surgical filament has a straight tensile strength of at least 50,000 psi and a Young's modulus below 250,000 psi.

2. The surgical filament of claim 1 wherein said filament is attached at least at one end to a needle.

3. The surgical filament of claim 1 wherein said filament is sterile.

4. The surgical filament of claim 1 wherein said block copolyetheramide contains at least one polyamide segment derived from laurolactam.

5. The surgical filament of claim 1 wherein said block copolyetheramide contains at least one polyamide segment derived from omega-amino-undecanoic acid.

6. The surgical filament of claim 1 wherein said block copolyetheramide contains at least one polyoxytetramethylene segment.

7. The surgical filament of claim 4 wherein said block copolyetheramide contains at least one polyoxytetramethylene segment.

8. The surgical filament of claim 5 wherein said block copolyetheramide contains at least one polyoxytetramethylene segment.

9. The surgical filament of claim 1 wherein said filament has a straight tensile strength of at least 75,000 psi and a Young's modulus below about 200,000 psi.

10. The surgical filament of claim 4 wherein said filament has a straight tensile strength of at least 75,000 psi and a Young's modulus below about 200,000 psi.

11. The surgical filament of claim 5 wherein said filament has a straight tensile strength of at least 75,000 psi and a Young's modulus below about 200,000 psi.

12. The surgical filament of claim 6 wherein said filament has a straight tensile strength of at least 75,000 psi and a Young's modulus below about 200,000 psi.

13. The surgical filament of claim 7 wherein said filament has a straight tensile strength of at least 75,000 psi and a Young's modulus below about 200,000 psi.

14. The surgical filament of claim 8 wherein said filament has a straight tensile strength of at least 75,000 psi and a Young's modulus below about 200,000 psi.

15. The surgical filament of claim 1 in the form of a fibrous prosthesis.

* * * * *